United States Patent
Kim et al.

(10) Patent No.: US 11,988,651 B2
(45) Date of Patent: May 21, 2024

(54) METABOLOME SAMPLING AND ANALYSIS METHOD FOR ANALYZING METABOLOME DURING SYNTHETIC GAS FERMENTATION OF SYNTHETIC GAS FERMENTATION MICROORGANISMS

(71) Applicants: Korea University Research and Business Foundation, Seoul (KR); Korea Institute of Science and Technology, Seoul (KR)

(72) Inventors: Kyoung Heon Kim, Seoul (KR); Young Soon Um, Seoul (KR); Jung Yeon Kim, Seoul (KR); Joongsuk Kim, Gwangmyeong-si (KR)

(73) Assignees: Korea University Research and Business Foundation, Seoul (KR); Korea Institute of Science and Technology, Seoul (KR)

( * ) Notice: Subject to any disclaimer, the term of this patent is extended or adjusted under 35 U.S.C. 154(b) by 881 days.

(21) Appl. No.: 16/975,581

(22) PCT Filed: Feb. 21, 2019

(86) PCT No.: PCT/KR2019/002146
§ 371 (c)(1),
(2) Date: Aug. 25, 2020

(87) PCT Pub. No.: WO2019/168300
PCT Pub. Date: Sep. 6, 2019

(65) Prior Publication Data
US 2020/0393427 A1    Dec. 17, 2020

(30) Foreign Application Priority Data
Feb. 28, 2018 (KR) .................. 10-2018-0024259

(51) Int. Cl.
*G01N 30/72* (2006.01)
*G01N 1/22* (2006.01)
(Continued)

(52) U.S. Cl.
CPC .......... *G01N 30/7206* (2013.01); *G01N 1/22* (2013.01); *G01N 30/06* (2013.01);
(Continued)

(58) Field of Classification Search
CPC ...... G01N 30/7206; G01N 1/22; G01N 30/06; G01N 30/8675; G01N 30/88;
(Continued)

(56) References Cited

U.S. PATENT DOCUMENTS 5,221,477 A * 6/1993 Melcher ................ G01N 30/08
                                                            210/490
5,445,966 A * 8/1995 Giese ...................... G01N 30/00
                                                            436/103
(Continued)

FOREIGN PATENT DOCUMENTS

JP       2011-7628 A       1/2011
KR       10-0818202 B1     3/2008
KR       10-2015-0146032 A 12/2015

OTHER PUBLICATIONS

Jae-In Lee, "GC/MS-based metabolomic analysis of Yersinia enterocolitica and its growth media", Journal of Agriculture & Life Science, 2015, pp. 199-207, vol. 49, No. 4.
(Continued)

*Primary Examiner* — David A Vanore
(74) *Attorney, Agent, or Firm* — Sughrue Mion, PLLC

(57) ABSTRACT

The present invention relates to a metabolome sampling and analysis method for analyzing metabolome during synthetic gas fermentation of a synthetic gas fermentation microorganisms, the method establishing an optimal condition for
(Continued)

metabolome sampling and enabling a glucose culture and a synthetic gas culture of the synthetic gas fermentation microorganisms to be distinguished by using a selected metabolomic biomarker.

1 Claim, 9 Drawing Sheets

(51) Int. Cl.
*G01N 30/06* (2006.01)
*G01N 30/86* (2006.01)
*G01N 30/88* (2006.01)
*G01N 33/497* (2006.01)

(52) U.S. Cl.
CPC ......... *G01N 30/8675* (2013.01); *G01N 30/88* (2013.01); *G01N 33/497* (2013.01); *G01N 2001/2244* (2013.01); *G01N 2030/062* (2013.01); *G01N 2030/8813* (2013.01); *G01N 2033/4977* (2013.01)

(58) Field of Classification Search
CPC ......... G01N 33/497; G01N 2001/2244; G01N 2030/062; G01N 2030/8813; G01N 2033/4977; G01N 30/72
See application file for complete search history.

(56) References Cited

U.S. PATENT DOCUMENTS

| 10,278,617 | B1* | 5/2019 | Satterfield | G01N 33/497 |
|---|---|---|---|---|
| 2004/0241721 | A1* | 12/2004 | Gjerde | G01N 1/40 536/25.4 |
| 2008/0234945 | A1* | 9/2008 | Walk | G16C 20/20 702/19 |
| 2011/0214487 | A1* | 9/2011 | Olesik | B01J 20/3295 73/61.54 |
| 2014/0261868 | A1* | 9/2014 | Wrench | G01N 30/22 220/23.91 |
| 2016/0046582 | A1* | 2/2016 | Frenkel | A61P 25/00 562/455 |
| 2016/0109417 | A1* | 4/2016 | Nunoshige | G01N 30/52 436/161 |
| 2018/0172714 | A1* | 6/2018 | Reisinger | G01N 33/94 |
| 2019/0041332 | A1* | 2/2019 | Thomas | A61B 5/082 |
| 2019/0195758 | A1* | 6/2019 | Alden | G01N 1/405 |
| 2019/0250178 | A1* | 8/2019 | Reisinger | G01N 33/94 |
| 2020/0393427 | A1* | 12/2020 | Kim | G01N 1/22 |

OTHER PUBLICATIONS

H. Richter et al., "Ethanol production in syngas-fermenting Clostridium ljungdahlii is controlled by thermodynamics rather than by enzyme expression", Energy and Environmental Science, 2016, pp. 2392-2399, vol. 9.

Anxela Fernandez-Naveira, "Glucose bioconversion profile in the syngas-metabolizing species *Clostridium carboxidivorans*", Bioresource Technology, 2017, pp. 552-559, vol. 244.

Daniel Amador-Noguez et al., "Metabolome Remodeling during the Acidogenic-Solventogenic Transition in Clostridium acetobutylicum", Applied and Environmental Microbiology, Nov. 2011, p. 7984-7997, vol. 77, No. 22.

Wael Sabra et al., "Fermentation of mixed substrates by Clostridium pasteurianum and its physiological, metabolic and proteomic characterizations", Microbial Cell Factories, 2016, pp. 1-14, vol. 15, No. 114.

Joshua D. Rabinowitz et al., "Acidic Acetonitrile for Cellular Metabolome Extraction from *Escherichia coli*", Analytical Chemistry, Aug. 15, 2007, pp. 6167-6173, vol. 79, No. 16.

Andre B. Canelas et al., "Quantitative Evaluation of Intracellular Metabolite Extraction Techniques for Yeast Metabolomics", Analytical Chemistry, Sep. 1, 2009, pp. 7379-7389, vol. 81, No. 17.

Min Hye Shin et al., "Evaluation of Sampling and Extraction Methodologies for the Global Metabolic Profiling of Saccharophagus degradans", Analytical Chemistry, Aug. 1, 2010, pp. 6660-6666, vol. 82, No. 15.

Sooah Kim et al., "Evaluation and Optimization of Metabolome Sample Preparation Methods for *Saccharomyces cerevisiae*", Analytical Chemistry, Jan. 4, 2013, pp. 2169-2176, vol. 85.

Sang-Hyun Lee et al., "Atmospheric vs. Anaerobic Processing of Metabolome Samples for the Metabolite Profiling of a Strict Anaerobic Bacterium, Clostridium acetobutylicum", Biotechnology and Bioengineering, Dec. 2014, pp. 2528-2536, vol. 111, No. 12.

Xavier Duportet et al., The biological interpretation of metabolomic data can be misled by the extraction method used, Metabolomics, 2012, 14 pgs., vol. 8, No. 3.

International Search Report for PCT/KR2019/002146 dated Jun. 10, 2019 (PCT/ISA/210).

* cited by examiner

METABOLOME SAMPLING AND ANALYSIS METHOD FOR ANALYZING METABOLOME DURING SYNTHETIC GAS FERMENTATION OF SYNTHETIC GAS FERMENTATION MICROORGANISMS

CROSS REFERENCE TO RELATED APPLICATIONS

This application is a National Stage of International Application No. PCT/KR2019/002146 filed Feb. 21, 2019, claiming priority based on Korean Patent Application No. 10-2018-0024259, filed Feb. 28, 2018, the entire disclosures of which are incorporated herein by reference.

TECHNICAL FIELD

The present invention relates to a metabolome sampling and analysis method for analyzing a metabolome during synthetic gas fermentation of a synthetic gas fermentation microorganisms.

BACKGROUND ART

Due to the importance of metabolome sampling in microorganisms, an optimization study has been conducted on metabolome sampling methods for metabolomic analysis in various microorganisms including Gram-negative bacteria such as *Saccharophagus degradans, Escherichia coli.*, and yeast, and studies on various mechanisms for changes in metabolomes have been conducted based on such optimized metabolome sampling methods (Rabinowitz J D and Kimball E. (2007) Anal Chem vol. 79, pp. 6167-6173; Shin M H et al (2010) Anal Chem vol. 82, pp. 6660-6666; Kim S et al (2013) Anal Chem vol. 85, pp. 2169-2176). In the case of the metabolome sampling method of anaerobic bacteria, a metabolome extraction method using methanol in the aerobic environment of *Clostridium acetobutylicum* has been reported (Lee S H et al (2014) Biotechnol Bioeng vol. 111, pp. 2528-2536), but in the case of a microorganism that fixes carbon, no optimization study on the metabolome sampling method has been reported.

Since synthetic gas fermentation microorganisms generate energy and grow by utilizing a metabolic circuit which is completely different from the metabolic circuit when using general sugars as a substrate (Richter Hetal (2016) Energy Environ Sci vol. 9, pp., 2392-2399), the types and amounts of metabolites differ significantly. Depending on the nature of the extraction solvent, the metabolome may have greatly different extraction efficiencies and show a difference in metabolomic profiling (Duportet X et al (2012) Metabolomics vol. 8, pp. 410-421; Canelas A B et al (2009) Anal Chem vol. 81, pp. 7379-7389). The difference in metabolomic profiling may limit or alter biological understanding or the understanding of the mechanism.

Therefore, there is a need for optimizing an extraction solvent which can reduce the degree of error in biological understanding or the understanding of the mechanism by increasing the efficiency of metabolome extraction during the culture of synthetic gas fermentation microorganisms and enabling reproducible extraction.

DISCLOSURE

Technical Problem

Thus, the present inventors extracted and qualitatively and quantitatively determined a metabolome specific to synthesis gas culture through a glucose culture and a synthesis gas culture of a synthetic gas fermentation microorganisms for the analysis of the specific metabolome of the synthetic gas fermentation microorganisms, and established an optimal metabolome extraction solvent capable of maximally extracting the metabolome based on the extraction efficiency and reproducibility in synthesis gas culture of such carbon-fixing microorganisms, thereby completing the present invention.

Therefore, an object of the present invention is to provide a kit for distinguishing a glucose culture and a synthetic gas culture of a synthetic gas fermentation microorganism.

Further, an object of the present invention is to provide a method for analyzing metabolomic differentiation for distinguishing a glucose culture and a synthetic gas culture of a synthetic gas fermentation microorganisms.

Technical Solution

The present invention provides a kit for distinguishing a glucose culture and a synthesis gas culture of a synthetic gas fermentation microorganisms, including a quantitative apparatus for at least one metabolite selected from the group consisting of palmitic acid, stearic acid, arachidic acid, heptadecanoic acid, 1-monopalmitin, alanine, N-methylalanine, adenosine, glycerol-1-phosphate, and valine.

In addition, the present invention provides a method for analyzing metabolomic differentiation for distinguishing a glucose culture and a synthetic gas culture of a synthetic gas fermentation microorganisms, including:

a metabolome sampling step of subjecting a biological sample of the synthetic gas fermentation microorganisms to fast filtration under an aerobic condition, washing the filtrate with water, and then extracting a metabolome using a mixed solvent of water, 2-propanol, and methanol as an extraction solvent.

Advantageous Effects

The present invention has effects of establishing an extraction solvent which is excellent in washing and extraction efficiencies using fast filtration and an optimal volume of solvent under an optimized metabolome sampling condition, that is, an aerobic condition for metabolomic analysis during synthetic gas fermentation of a synthetic gas fermentation microorganisms, and providing a metabolomic biomarker which enables a glucose culture and a synthetic gas culture of the synthetic gas fermentation microorganisms to be distinguished by using various statistical analyses such as metabolome comparison analysis using GC/TOF MS, partial least squares discriminant analysis (PLS-DA), hierarchical clustering analysis (HCA), a coefficient of variation (CV), principal component analysis (PCA), a receiver operating characteristic curve (ROC curve), and confidence interval analysis.

The present invention is expected to be utilized for studying various mechanisms through metabolomic analysis of a synthetic gas fermentation microorganism. Further, by demonstrating the need for an optimal metabolome sampling method suitable for each microorganism, the present invention can be used to be applied to the optimization of a metabolome sampling method for other microorganisms.

BEST MODE

The present invention relates to a kit for distinguishing a glucose culture and a synthesis gas culture of a synthetic gas fermentation microorganisms, including a quantitative apparatus for at least one metabolite selected from the group consisting of palmitic acid, stearic acid, arachidic acid, heptadecanoic acid, 1-monopalmitin, alanine, N-methylalanine, adenosine, glycerol-1-phosphate, and valine.

The present inventors performed a biomarker discovery study capable of distinguishing a glucose culture and a synthetic gas culture of a synthetic culture fermentation microorganisms by washing using water and extracting a metabolome using pure ethanol after fast filtration under an aerobic condition, comparing and analyzing the difference in metabolomic profile between the glucose culture and the synthetic gas culture using GC/TOF MS, and using the difference, in order to find a biomarker which distinguishes the glucose culture and the synthetic gas culture of the synthetic gas fermentation microorganism.

As a result, 82 metabolites that can be classified into amines, amino acids, fatty acids, organic acids, phosphoric acids, sugars, and the like were identified, Among them, organic acids, fatty acids, and sugars were most frequently detected, followed by amino acids, amines, phosphoric acids, and the like.

Figure 2:
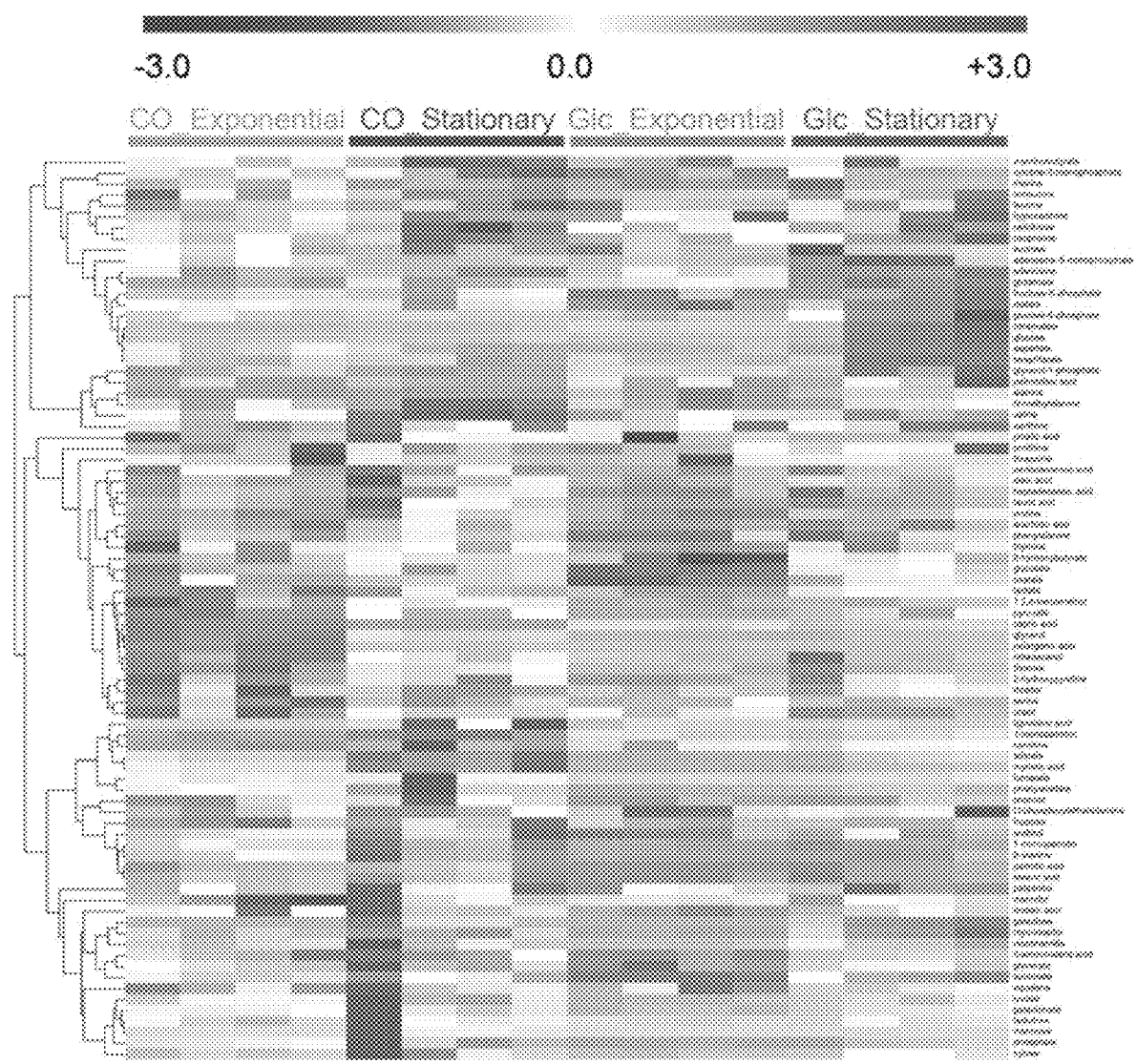
FIG. 2 illustrates metabolomic profiles (Glc_Exponential: a metabolomic analysis result of the exponential phase in the glucose culture; Glc_Stationary: a metabolomic analysis result of the stationary phase in the glucose culture; CO_Exponential: a metabolomic analysis result of the exponential phase in the synthetic gas culture; CO_Stationary: a metabolomic analysis result of the stationary phase in the synthetic gas phase) in each phase during a glucose culture and a synthetic gas culture of a synthetic gas fermentation microorganisms using HCA.

When biological samples were compared by performing sampling at the exponential phase and the stationary phase of the glucose culture and synthetic gas culture of the synthetic gas fermentation microorganisms, respectively, a clear difference in metabolomic profile of the glucose culture and the synthetic gas culture of the synthetic gas fermentation microorganism was confirmed through partial least squares discriminant analysis (PLS-DA), and based on the loading values of the PLS-DA model for each metabolite, 5 metabolites each having the largest positive values and 5 metabolites each having the largest negative values were selected, and 10 metabolites were selected as novel biomarker candidate materials (FIG. 2). It was confirmed that each metabolite was an appropriate candidate biological marker by exhibiting a statistically clear difference in the glucose culture and the synthetic gas culture of the synthetic gas fermentation microorganism. Further, it was intended to show the difference of an individual metabolite between the glucose culture and the synthetic gas culture of the synthetic gas fermentation microorganisms by performing HCA, and as a result, a clear difference of the individual metabolite for each culture was confirmed.

In addition, in order to distinguish the glucose culture and the synthetic gas culture of the synthetic gas fermentation microorganisms using the candidate metabolite, a model using PCA was generated, and the model generated using 10 metabolites showed a result of completely classifying metabolites of each culture condition. Furthermore, a verification was performed by applying a ROC curve to the model. As a result, it was possible to verify that the model had a high statistical significance, and thus was suitable for the metabolome classification during the glucose culture and the synthetic gas culture of the synthetic gas fermentation microorganisms.

As used herein, the term "synthetic gas fermentation microorganisms" refers to *Clostridum carboxidivorans*, and specifically includes *Clostridium carboxidivorans* P7.

In particular, the synthetic gas fermentation microorganism in the glucose culture shows a tendency that alanine, N-methylalanine, adenosine, glycerol-1-phosphate, and valine increase in the metabolome and a tendency that palmitic acid, stearic acid, arachidic acid, heptadecanoic acid, and 1-monopalmitin decrease in the metabolome.

Further, the synthetic gas fermentation microorganism in the synthetic gas culture shows a tendency that palmitic acid, stearic acid, arachidic acid, heptadecanoic acid, and 1-monopalmitin increase in the metabolome and a tendency that alanine, N-methylalanine, adenosine, glycerol-1-phosphate, and valine decrease in the metabolome.

The increasing or decreasing tendency refers to an increase or decrease in metabolite concentration, and the term increase in metabolite concentration means that the metabolite concentration in the synthetic gas fermentation microorganisms during the synthetic gas culture is significantly increased enough to be measurable compared to that during the glucose culture, and as used herein, the term decrease in metabolite means that the metabolite concentration in the synthetic gas fermentation microorganisms during the synthetic gas culture is significantly decreased enough to be measurable compared to that during the glucose culture.

The quantitative apparatus included in the kit of the present invention may be a chromatograph/mass spectrometer.

The chromatography used in the present invention includes gas chromatography, liquid-solid chromatography (LSC), paper chromatography (PC), thin-layer chromatography (TLC), gas-solid chromatography (GSC), liquid-liquid chromatography (LLC), foam Chromatography (FC), emulsion chromatography (EC), gas-liquid chromatography (GLC), ion chromatography (IC), gel filtration chromatography (GFC), or gel permeation chromatography (GPC), but any quantitative chromatography typically used in the art may be used without being limited thereto. Preferably, the chromatography used in the present invention may be a gas chromatography/time-of-flight mass spectrometry (GC/TOF MS) analysis device.

The respective components in the metabolome of the present invention are separated in gas chromatography, and constituent components are confirmed through not only exact molecular weight information, but also structural information (elemental composition) using information obtained via TOF MS.

The present invention also includes a method for analyzing metabolomic differentiation for distinguishing a glucose culture and a synthetic gas culture of a synthetic gas fermentation microorganisms.

The method for analyzing metabolomic differentiation is a method for analyzing the distinction between the exponential phase and the stationary phase during the glucose culture and the exponential phase and the stationary phase during the synthetic gas culture, and first, the method is subjected to a metabolome sampling step including a quenching process and a metabolome extraction process.

The metabolome sampling is a process of subjecting a biological sample of an anaerobic microorganisms to fast filtration under an aerobic condition, washing a filtered material with water, and then extracting a metabolome using, as an extraction solvent, a mixed solvent of acetonitrile and water, a mixed solvent of acetonitrile, methanol, and water, or a mixed solvent of water, 2-propanol, and methanol. In this case, the water used in the washing is preferably used in an amount of 3 parts by volume to 7 parts by volume based on a 1 volume ratio of an anaerobic bacterial liquid, and as the extraction solvent, a mixed solvent of water, 2-propanol, and methanol is preferred in terms of extraction efficiency and reproducibility. In particular, it is more preferred to use a mixed solvent in which water, 2-propanol, and methanol are mixed at 2:2:5 (v/v/v).

As an exemplary embodiment of the present invention, 86 metabolites including amines, amino acids, sugars and sugar alcohols, fatty acids, phosphoric acids, organic acids, and the like were identified.

The extracted metabolome in the metabolome sampling step is subjected to the following analysis steps:
  further including: analyzing the extracted metabolome with a gas chromatography/time-of-flight mass spectrometry (GC/TOF MS) analysis device;
  converting a GC/TOF MS analysis result into statistically processable values; and
  verifying the distinction between the two biological sample groups by using the converted values.

Next, in order to compare the profiling differences of the metabolome, a metabolomic biomarker which shows a significant difference between the two biological sample groups is selected, analyzed, and verified by performing a partial least squares discriminant analysis (PLS-DA).

As an exemplary embodiment, in the analysis method of the present invention, the converting of the GC/TOF MS analysis result into statistically processable values determines, as a representative value of unit time, the largest value of an area or height of a chromatogram peak appearing during the unit time by dividing the total analysis time by a unit time interval.

The statistically verifying of the distinction between two biological sample groups by using the converted values analyzes and verifies a metabolomic biomarker which shows a significant difference between the two biological sample groups by performing a partial least squares discriminant analysis (PLS-DA).

The metabolomic biomarker differentiates a glucose culture and a synthetic gas culture of a synthetic gas fermentation microorganisms.

The metabolomic biomarker includes palmitic acid, stearic acid, arachidic acid, heptadecanoic acid, 1-monopalmitin, alanine, N-methylalanine, adenosine, glycerol-1-phosphate, and valine.

A positive loading value of the partial least squares discriminant analysis (PLS-DA) shows an increasing tendency of the metabolomic biomarker, and a negative loading value of the partial least squares discriminant analysis (PLS-DA) shows a decreasing tendency of the metabolomic biomarker.

It is determined that a positive loading value of the PLS-DA shows an increasing tendency of the metabolomic biomarker, and a negative loading value of the PLS-DA shows a decreasing tendency of the metabolomic biomarker. According to an exemplary embodiment of the present invention, as a biomarker for differentiating a metabolome during the glucose culture and the synthetic gas culture of the synthetic gas fermentation microorganisms, it is possible to use palmitic acid, stearic acid, arachidic acid, heptadecanoic acid, 1-monopalmitin, alanine, N-methylalanine, adenosine, glycerol-1-phosphate, and valine.

The biomarkers may show a tendency that palmitic acid, stearic acid, arachidic acid, heptadecanoic acid, and 1-monopalmitin increase in the synthetic gas fermentation during the synthetic gas culture and a tendency that alanine, N-methylalanine, adenosine, glycerol-1-phosphate, and valine decrease in the synthetic gas fermentation during the synthetic gas culture.

Hereinafter, the present invention will be described in more detail through the Examples according to the present invention, but the scope of the present invention is not limited by the Examples suggested below.

MODES OF THE INVENTION

Hereinafter, the present invention will be described in further detail with reference to examples according to the present invention, but the scope of the present invention is not limited to the following examples.

EXAMPLES

Reference Example 1: Strain, Medium, and Culture Conditions

A seed culture solution was obtained by culturing *C. carboxidivorans* P7 in a 2× yeast extract, tryptone, and glucose (YTG) medium (Table 1). Cells were harvested when the $OD_{600}$ reached 2.0 to 2.5 (considered as a middle exponential phase). The cells were washed twice with a modified P7 medium (Table 1) and inoculated with 5 mL of the modified P7 medium in a 25-mL serum bottle as a main culture (10%, v/v). For CO fermentation, 1.5 bar was applied to a headspace of the serum bottle using a gas mixture (10% $H_2$, 70% CO, 20% $CO_2$, v/v/v, Air Korea, Seoul, Korea), and the cells were cultured at 37° C. and 200 rpm. For glucose fermentation, 5 mL of the modified P2 medium (MP2) was used for the main culture in the 25-mL serum bottle (Phillips J R Atiyeh H K, Tanner R S, Torres J R, Saxena J, Wilkins M R, Huhnke R L. 2015. Butanol and hexanol production in *Clostridium carboxidivorans* syngas fermentation: medium development and culture techniques. Bioresour Technol 190:114-121.). The cells were inoculated into a glucose medium and cultured at 37° C. with shaking at 200 rpm. All the media were anaerobically prepared after being purged with argon (99.9%, w/w).

TABLE 1

Composition of YTG, MP2 and P2 media

| Media | Composition | Concentration (g/L) |
|---|---|---|
| YTG (2X) | Glucose | 5 |
| | Peptone | 16 |
| | Yeast extract | 10 |
| | NaCl | 0.9 |
| P7 | Glucose | 5 |
| | $K_2HPO_4$ | 0.5 |
| | $KH_2PO_4$ | 0.5 |
| | $(NH_4)_2SO_4$ | 2 |
| | $MnSO_4 \cdot H_2O$ | 0.01 |
| | $MgSO_4 \cdot 7H_2O$ | 0.2 |
| | $FeSO_4 \cdot 7H_2O$ | 0.01 |
| | NaCl | 0.01 |
| | Yeast extract | 6 |
| | MES | 19.52 |
| MP2 | Yeast extract | 0.5 |
| | MES | 10 |
| | KOH | 1.165 |
| | $NH_4Cl$ | 2 |
| | $CaCl_2 \cdot 2H_2O$ | 0.08 |
| | $MgSO_4 \cdot 7H_2O$ | 0.4 |
| | KCl | 0.2 |
| | $KH_2PO_4$ | 0.2 |
| | $MnSO_4 \cdot H_2O$ | 0.01 |
| | $NaMoO_4 \cdot 2H_2O$ | 0.002 |
| | Resazurin | 0.001 |
| | Cysteine | 0.2 |

The synthetic gas fermentation strain used in the following Examples is *Clostridium carboxidivorans* P7.

Example 1: Metabolomic Profiling in Exponential Phase and Stationary Phase During Glucose Culture and Synthetic Gas Culture of Synthetic Gas Fermentation Strain Using PLS-DA and HCA In the exponential phase and the stationary phase of a glucose culture and a synthetic gas culture of a synthetic gas fermentation microorganisms, 2 ml of each bacterial liquid was sampled, subjected to a fast filtration method in the atmosphere, and washed using 10 ml of distilled water. The filtrate was mixed with 10 m of pure methanol conventionally used as an extraction solvent, and metabolic activity was stopped by freezing the resulting mixture in liquid nitrogen. Thereafter, after the mixed solution was thawed on ice, the mixed solution was subjected to ultrasonication for 5 minutes, vortexed for 3 minutes, and then centrifuged at 16,100 g and 4° C. for 10 minutes, and then the supernatant was completely dried and analyzed with GC/TOF MS.

When the metabolome during the glucose culture and the synthetic gas culture of the synthetic gas fermentation microorganisms was extracted using methanol and the GC/TOF MS-analyzed data was processed, 82 metabolites including amines, amino acids, sugars and sugar alcohols, fatty acids, phosphoric acids, organic acids, and the like were identified (Table 2).

In order to compare the metabolomic profiling difference during the glucose culture and the synthetic gas culture of the synthetic gas fermentation microorganisms, PLS-DA and HCA were performed using the 82 metabolites.

Figure 1:
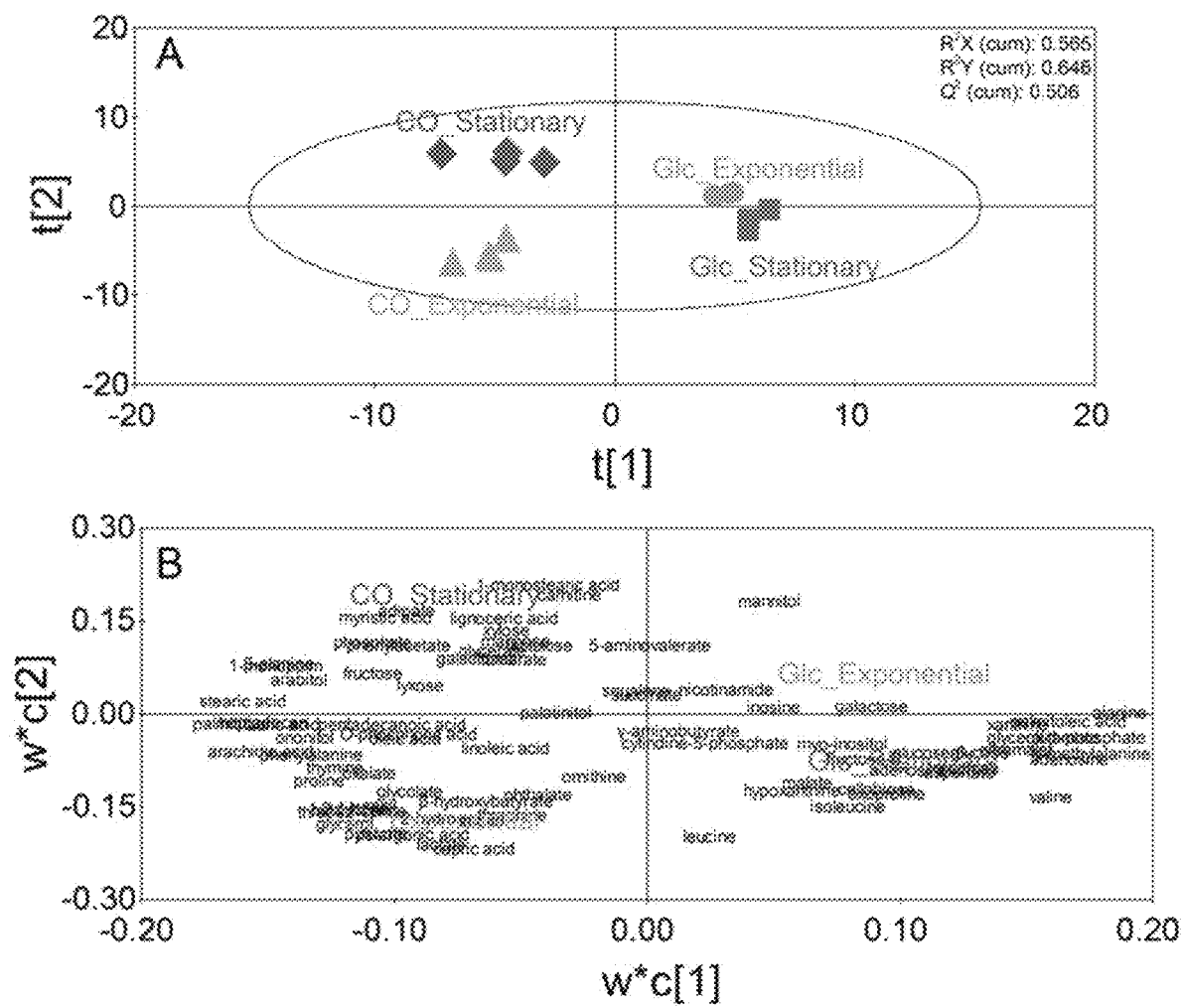
FIG. 1 illustrates metabolomic profiles (Glc_Exponential: a metabolomic analysis result of the exponential phase in the glucose culture; Glc_Stationary: a metabolomic analysis result of the stationary phase in the glucose culture; CO_Exponential: a metabolomic analysis result of the exponential phase in the synthetic gas culture; CO_Stationary: a metabolomic analysis result of the stationary phase in the synthetic gas culture, A: score plot; B: loading plot) in each phase during a glucose culture and a synthetic gas culture of a synthetic gas fermentation microorganisms using PLS-DA.

Results of the PLS-DA showed that regardless of the exponential phase and the stationary phase, the metabolomic profiles were clearly different by exhibiting positive values and negative values based on the t[1] axis during the glucose culture and the synthetic gas culture, respectively (FIG. 1, Table 3).

Further, as a result of examining the increase and decrease in individual metabolites with HCA, the metabolite at the top of HCA during the glucose culture showed a clear difference because the metabolites in the middle and the bottom showed high intensities and distinct differences during the synthetic gas fermentation (FIG. 2). Therefore, it was confirmed that a large difference in metabolomic profiling appeared. Through this, it was confirmed that the synthetic gas fermentation microorganisms had a unique metabolome pattern during the synthetic gas culture.

TABLE 2

82 metabolites extracted using pure methanol in glucose and synthetic gas cultures of synthetic gas fermentation strain
Identification of metabolites

| Amines | | |
|---|---|---|
| 2-hydroxypyridine | adenosine | carnitine |
| hypoxanthine | inosine | nicotinamide |
| O-phosphorylethanolamine | thymine | uracil |
| xanthine | | |

| Amino acids | | |
|---|---|---|
| 5-aminovaleric acid | alanine | glutamate |
| isoleucine | leucine | N-methylalanine |
| ornithine | oxoproline | phenylalanine |
| proline | serine | threonine |
| valine | β-alanine | |

TABLE 2-continued 82 metabolites extracted using pure
methanol in glucose and synthetic gas cultures
of synthetic gas fermentation strain
Identification of metabolites

Fatty acids

| | | |
|---|---|---|
| 1-monopalmitin | 1-monostearin | arachidic acid |
| capric acid | heptadecanoic acid | lauric acid |
| lignoceric acid | linoleic acid | myristic acid |
| octadecanol | oleic acid | palmitic acid |
| palmitoleic acid | pelargonic acid | pentadecanoic acid |
| squalene | stearic acid | |

Organic acids

| | | |
|---|---|---|
| adipate | aspartate | citramalate |
| fumarate | galactonate | glycerate |
| glycolate | lactate | malate |
| oxalate | phenylacetate | phthalic acid |
| pyruvate | succinate | terephtalate |
| β-hydroxybutyrate | γ-aminobutyrate | |

Sugars and sugar alcohols

| | | |
|---|---|---|
| arabitol | cellobiose | fructose |
| galactose | glucose | glycerol |
| lactulose | lyxose | mannitol |
| mannose | myo-inositol | ononitol |
| palatinitol | sucrose | threitol |
| threose | xylose | |

Phosphates

| | | |
|---|---|---|
| adenosine-5-monophosphate | cytindine-5-monophosphate | fructose-6-phosphate |
| glucose-6-phosphate | glycerol-1-phosphate | phosphate |

Others 1,2,4-benzenetriol

TABLE 3

| Metabolites | Loading 1 | Loading 2 |
|---|---|---|
| 1,2,4-benzenetriol | −0.136 | −0.145 |
| 1-monopalmitin | −0.168 | 0.086 |
| 1-monostearin | −0.070 | 0.216 |
| 2-hydroxypyridine | −0.100 | −0.160 |
| 5-aminovalerate | −0.025 | 0.118 |
| adenosine | 0.149 | −0.065 |
| adenosine-5-monophosphate | 0.086 | −0.082 |
| adipate | −0.109 | 0.175 |
| alanine | 0.174 | 0.009 |
| arabitol | −0.151 | 0.063 |
| arachidic acid | −0.176 | −0.057 |
| aspartate | 0.107 | −0.086 |
| β-alanine | −0.162 | 0.089 |
| β-hydroxybutyrate | −0.092 | −0.133 |
| capric acid | −0.087 | −0.210 |
| carnitine | −0.046 | 0.202 |
| cellobiose | 0.073 | −0.115 |
| citramalate | 0.129 | −0.049 |
| cytindine-5-monophosphate | −0.012 | −0.039 |
| fructose | −0.123 | 0.075 |
| fructose-6-phosphate | 0.069 | −0.065 |
| fumarate | −0.068 | 0.097 |
| galactonate | −0.086 | 0.098 |
| galactose | 0.072 | 0.020 |
| &gamma-aminobutyrate | −0.014 | −0.020 |
| glucose | 0.118 | −0.054 |
| glucose-6-phosphate | 0.095 | −0.055 |
| glutamate | 0.148 | −0.030 |
| glycerate | −0.077 | 0.110 |
| glycerol | −0.130 | −0.174 |
| glycerol-1-phosphate | 0.149 | −0.030 |
| glycolate | −0.109 | −0.118 |
| heptadecanoic acid | −0.172 | −0.006 |
| hypoxanthine | 0.036 | −0.116 |
| inosine | 0.037 | 0.018 |

TABLE 3-continued

| Metabolites | Loading 1 | Loading 2 |
|---|---|---|
| isoleucine | 0.062 | −0.142 |
| lactate | −0.094 | −0.203 |
| lactulose | −0.058 | 0.120 |
| lauric acid | −0.162 | −0.010 |
| leucine | 0.012 | −0.191 |
| lignoceric acid | −0.080 | 0.162 |
| linoleic acid | −0.075 | −0.048 |
| lyxose | −0.101 | 0.054 |
| malate | 0.051 | −0.103 |
| mannitol | 0.034 | 0.190 |
| mannose | −0.068 | 0.126 |
| myo-inositol | 0.057 | −0.042 |
| myristic acid | −0.124 | 0.164 |
| nicotinamide | 0.010 | 0.047 |
| N-methylalanine | 0.154 | −0.057 |
| octadecanol | −0.135 | −0.147 |
| oleic acid | −0.112 | −0.032 |
| ononitol | −0.149 | −0.031 |
| O-phosphorylethanolamine | −0.123 | −0.026 |
| ornithine | −0.036 | −0.093 |
| oxalate | −0.123 | −0.087 |
| oxoproline | 0.077 | −0.120 |
| palatinitol | −0.052 | 0.010 |
| palmitic acid | −0.182 | −0.008 |
| palmitoleic acid | 0.141 | −0.005 |
| pelargonic acid | −0.118 | −0.186 |
| pentadecanoic acid | −0.132 | −0.010 |
| phenylacetate | −0.121 | 0.119 |
| phenylalanine | −0.155 | −0.059 |
| phosphate | −0.126 | 0.125 |
| phthalic acid | −0.059 | −0.123 |
| proline | −0.142 | −0.100 |
| pyruvate | −0.122 | −0.174 |
| serine | −0.116 | −0.149 |
| squalene | −0.020 | 0.046 |
| stearic acid | −0.179 | 0.029 |
| succinate | −0.017 | 0.039 |
| sucrose | 0.114 | −0.080 |
| terephthalic acid | 0.109 | −0.079 |
| threitol | −0.077 | −0.165 |
| threonine | −0.069 | −0.156 |
| threose | −0.140 | −0.150 |
| thymine | −0.137 | −0.079 |
| uracil | −0.117 | −0.139 |
| valine | 0.149 | −0.126 |
| xanthine | 0.132 | −0.009 |
| xylose | −0.067 | 0.143 |

Example 2: Selection of Main Metabolite Showing Difference in Glucose Culture and Synthetic Gas Culture of Synthetic Gas Fermentation Strain In order to select a representative metabolite showing the difference in glucose culture and synthetic gas culture of a synthetic gas fermentation strain, using the PLS-DA analysis model from Example 1, from the positive and negative loading values in the model, 5 metabolites respectively having the largest positive and negative values were calculated and a total of 10 metabolites were selected (Table 4).

TABLE 4

Loading values of 10 main metabolites showing difference
in glucose culture and synthetic gas culture

| Metabolites | Loading values |
|---|---|
| palmitic acid | −0.182 |
| stearic acid | −0.179 |
| arachidic acid | −0.176 |
| heptadecanoic acid | −0.172 |
| 1-monoalmitin | −0.168 |
| alanine | 0.149 |

TABLE 4-continued

Loading values of 10 main metabolites showing difference in glucose culture and synthetic gas culture

| Metabolites | Loading values |
|---|---|
| N-methylalanine | 0.149 |
| adenosine | 0.149 |
| glycerol-1-phosphate | 0.154 |
| valine | 0.174 |

Example 3: Selection of Optimal Extraction Solvent for Metabolomic Analysis of Synthetic Gas Fermentation Microorganisms In order to obtain a metabolome sample in the exponential phase and the stationary phase during the synthetic gas culture of the synthetic gas fermentation microorganism, after 2 mL of a bacterial liquid was sampled under an aerobic condition, a metabolome was obtained in each phase of the synthetic gas fermentation microorganism using a fast filtration method, and then washing the filtrate with 10 mil of water, and then the filtrate was mixed with 10 ml of each solvent of 50ACN (acetonitrile-water=1:1, v/v), AMW (acetonitrile-methanol-water=2:1:1, v/v/v), PM (pure methanol), WiPM (water-2-propanol-methanol=2:2:5, v/v/v) as an extraction solvent, and metabolic activity was stopped by freezing the resulting mixture in liquid nitrogen. Thereafter, after the mixed solution was thawed on ice, the mixed solution was subjected to ultrasonication for 5 minutes, vortexed for 3 minutes, and then centrifuged at 16,100 g and 4° C. for 10 minutes, and then the supernatant was completely dried and analyzed with GC/TOF MS. The extraction efficiencies were compared and analyzed by analysis with GC/TOF-MS.

When the metabolome during the synthetic gas culture of the synthetic gas fermentation microorganisms was extracted using 4 different extraction solvents and the GC/TOF MS-analyzed data was processed, 86 metabolites including amines, amino acids, sugars and sugar alcohols, fatty acids, phosphoric acids, organic acids, and the like were identified (Table 5).

Figure 3:
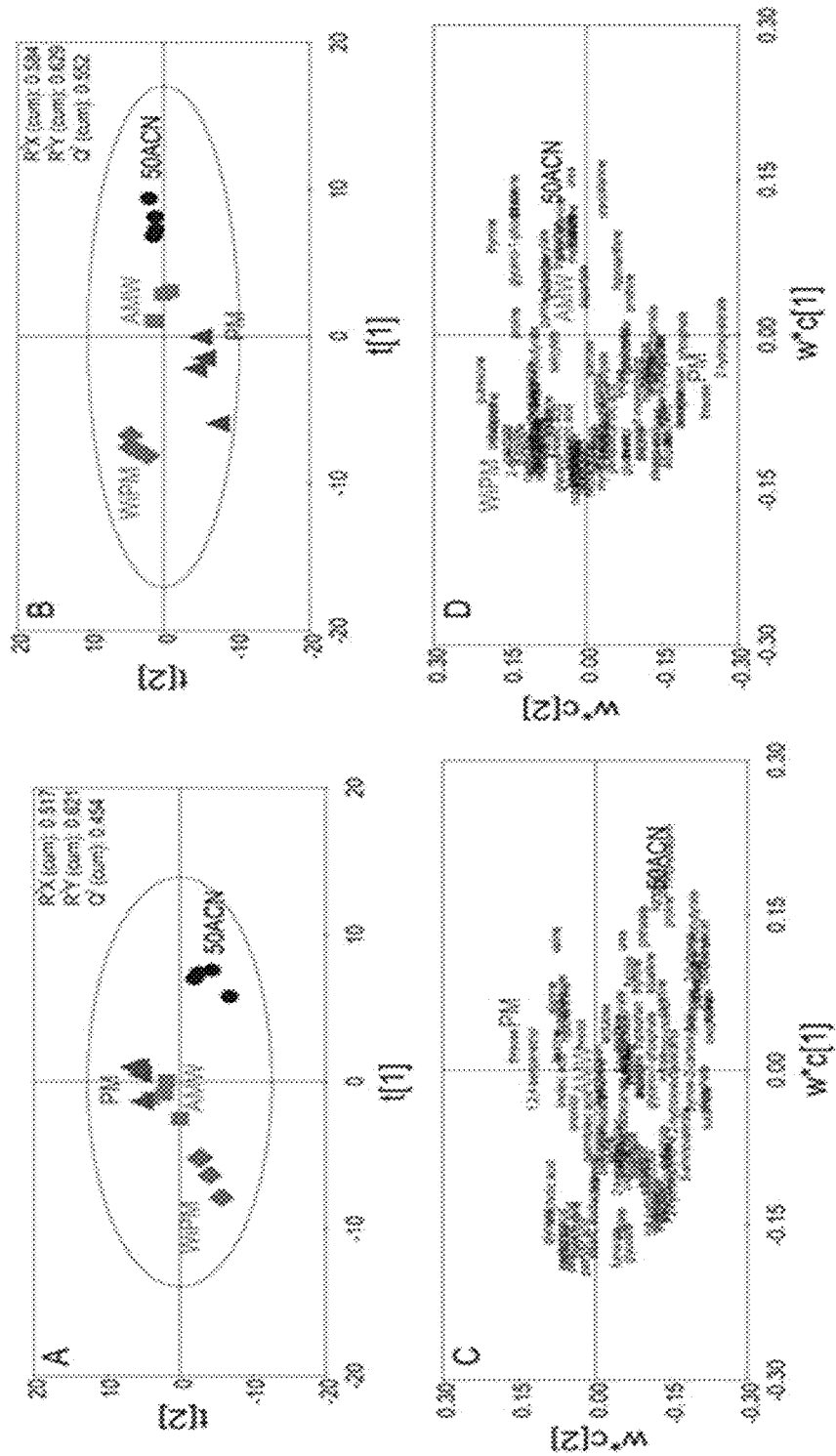
FIG. 3 illustrates metabolomic profiles (50ACN (acetonitrile-water=1:1, v/v), AMW (acetonitrile-methanol-water=2:1:1, v/v/v), PM (pure methanol), WiPM (water-2-propanol-methanol=2:2:5, v/v/v, A, C: the exponential phase in the synthetic gas culture, B, D: the stationary phase in the synthetic gas fermentation) when different extraction solvents are used in the synthetic gas culture of the synthetic gas fermentation microorganisms using PLS-DA.
Figure 4A:
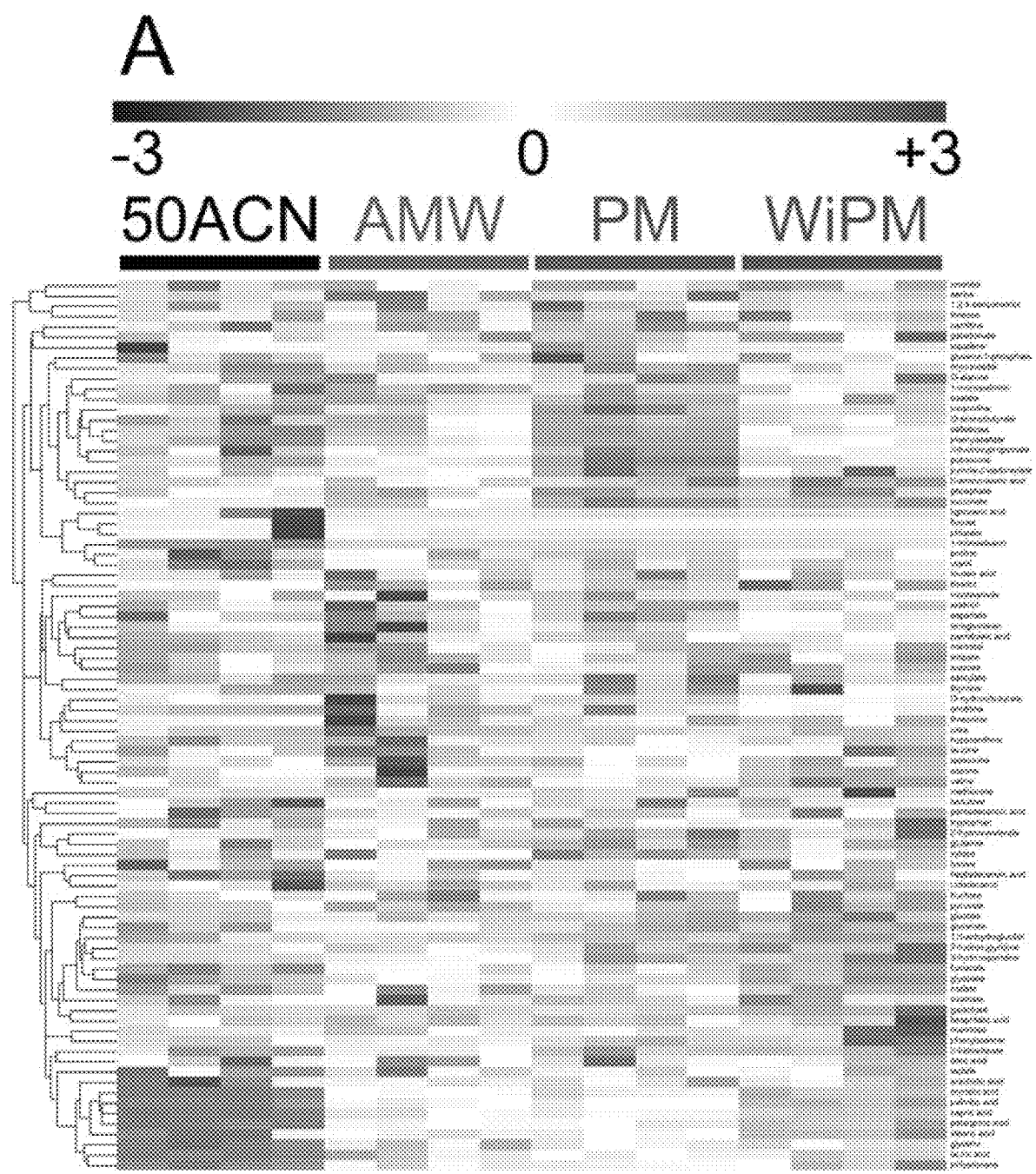
FIGS. 4A and 4B illustrate metabolomic profiles (50ACN: acetonitrile:water=1:1; AMW: acetonitrile:methanol:water=2:2:1; PM; pure methanol; WiPM: water:2-propanol:methanol=2:2:5, A: the exponential phase in the synthetic gas culture, B: the stationary phase in the synthetic gas culture) when different extraction solvents are used in the synthetic gas culture of the synthetic gas fermentation microorganisms using HCA.
Figure 4B:
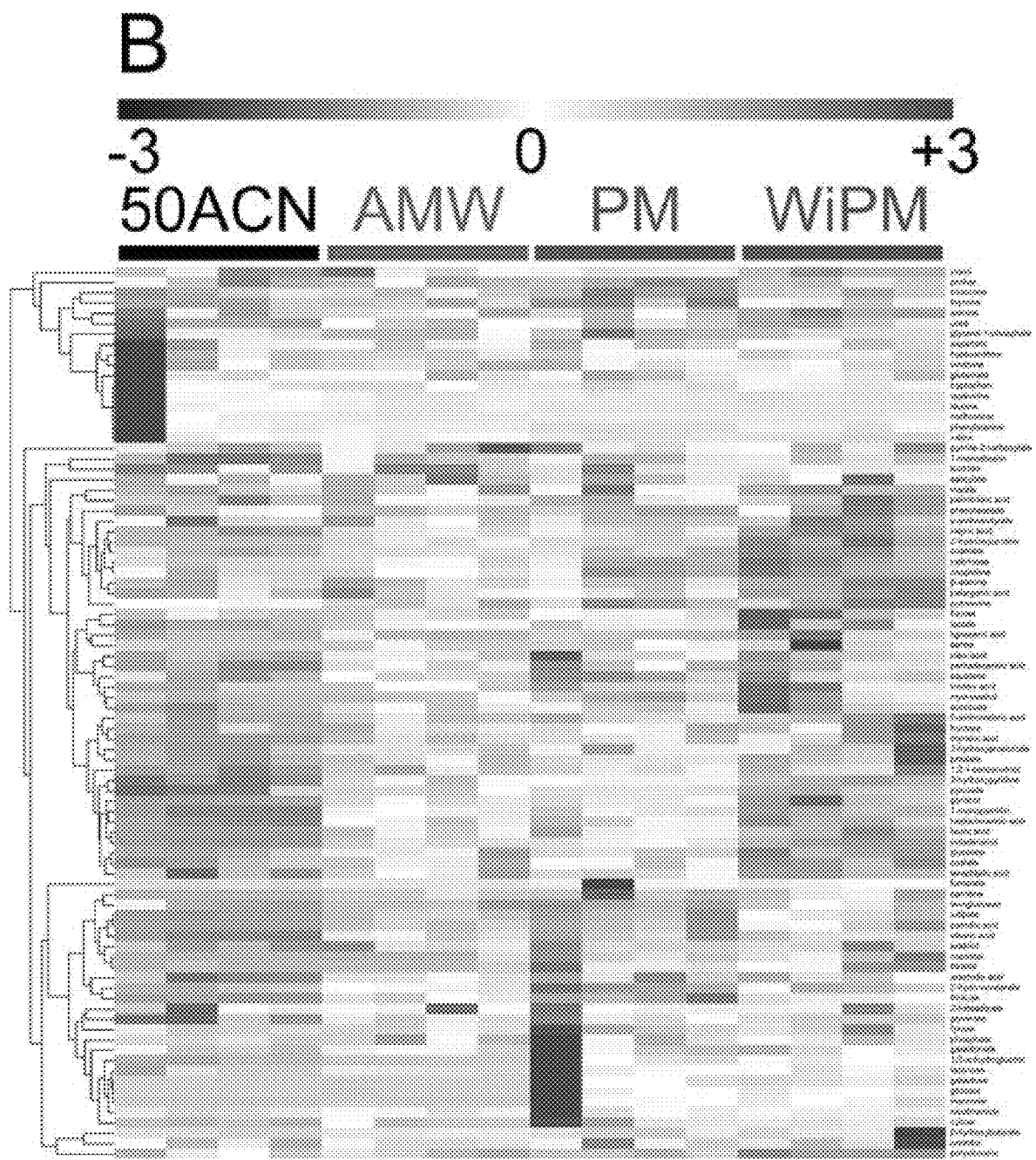
Figure 5:
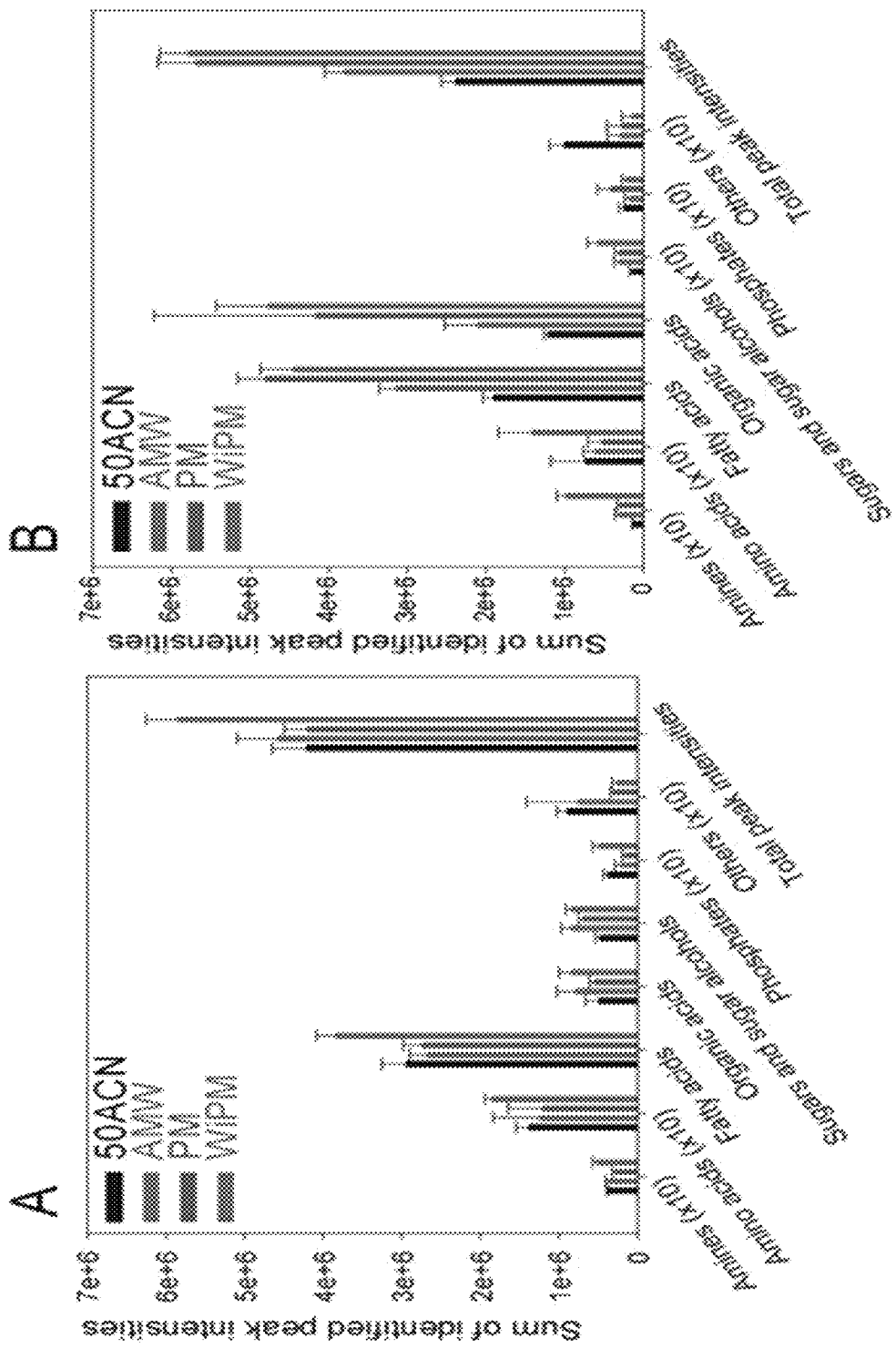
FIG. 5 illustrates metabolome extraction efficiency comparisons (50ACN (acetonitrile-water=1:1, v/v), AMW (acetonitrile-methanol-water=2:1:1, v/v/v), PM (pure methanol), WiPM (water-2-propanol-methanol=2:2:5, v/v/v, A: the exponential phase in the synthetic gas culture, B: the stationary phase in the synthetic gas culture) according to each extraction solvent in the synthetic gas culture of the synthetic gas fermentation microorganisms using the peak intensity.
Figure 6:
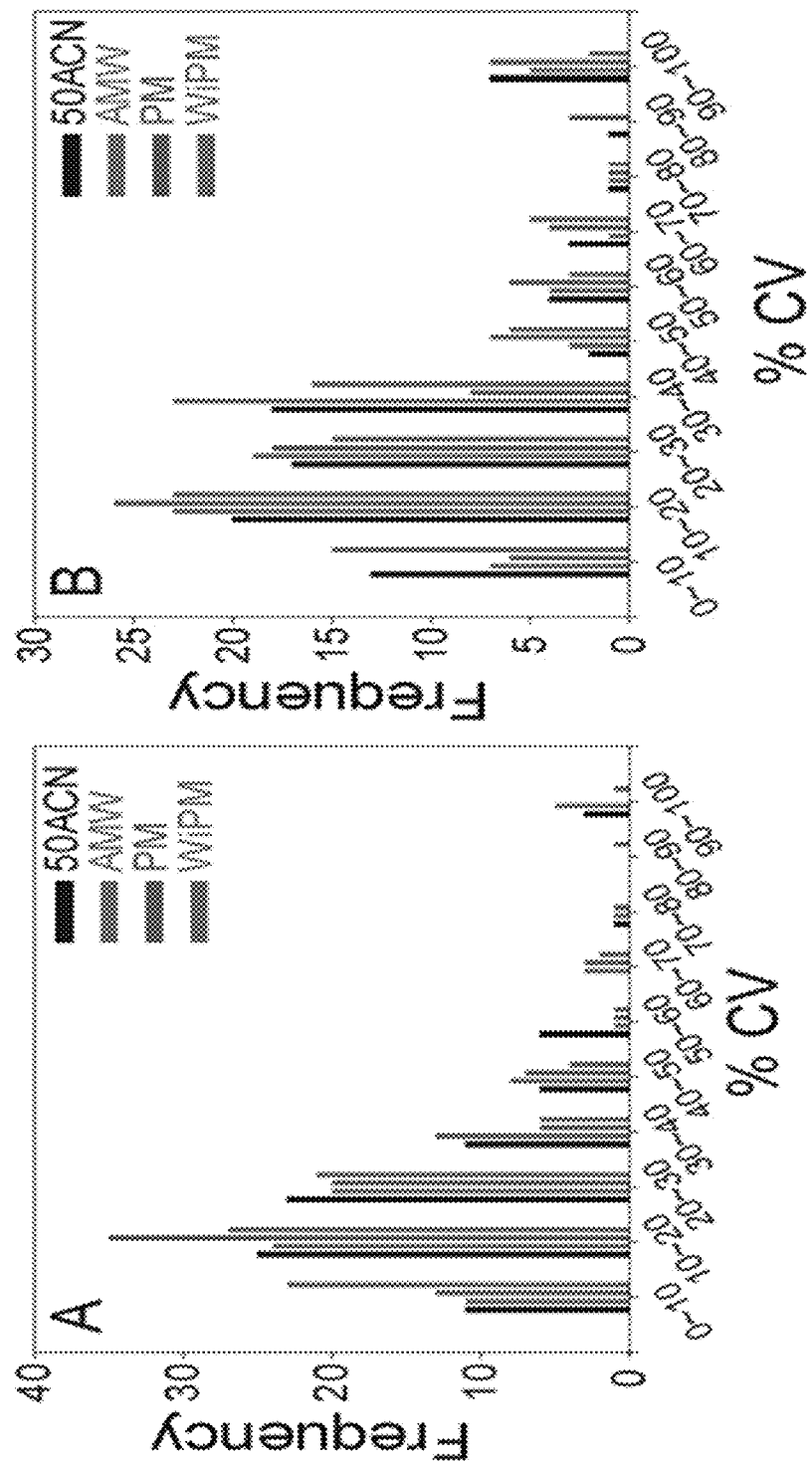
FIG. 6 illustrates metabolome extraction efficiency comparisons (50ACN (acetonitrile-water=1:1, v/v), AMW (acetonitrile-methanol-water=2:1:1, v/v/v), PM (pure methanol), WiPM (water-2-propanol-methanol=2:2:5, v/v/v, A: the exponential phase in the synthetic gas fermentation, B: the stationary phase in the synthetic gas fermentation) according to each extraction solvent in the synthetic gas culture of the synthetic gas fermentation microorganisms using the coefficient of variation (% CV).

As shown in FIGS. 3 and 4 and Table 6, it could be confirmed that in each phase, there is a difference in metabolomic profiling depending on the extraction solvent, and it could be confirmed that the extraction efficiency was also different. Since the qualitatively and relatively quantitatively analyzed peak intensity was the highest in the WiPM in the exponential phase and the stationary phase of the synthetic gas fermentation microorganism, it could be seen that the overall extraction efficiency of the metabolome was highest in the WiPM (FIG. 5). Further, when the reproducibility depending on the extraction solvent in the exponential phase and the stationary phase of the synthetic gas fermentation microorganism was examined, it could be seen that the reproducibility was the highest because all lowest % CV values were recorded in the WiPM (FIG. 6). Through this, WiPM was selected as an optimal solvent based on the extraction efficiency and reproducibility during the extraction of a metabolome for metabolomic analysis of a synthetic gas fermentation microorganisms.

TABLE 5

86 metabolites extracted using 4 different extraction solvents(50ACN, AMW, PM, WiPM) in exponential phase and stationary phase during synthetic gas fermentation of synthetic gas fermentation strain Identified metabolites

| Amines | | |
|---|---|---|
| 2-hydroxypyridine | 3-hydroxypyridine | carnitine |
| hypoxanthine | thymine | uracil |
| Amino acids | | |
| 5-aminovaleric acid | alanine | β-alanine |
| glutamate | isoleucine | leucine |
| methionine | ornithine | oxoproline |
| phenylalanine | proline | serine |
| threonine | tryptophan | valine |
| Fatty acids | | |
| 1-monopalmitin | 1-monostearin | arachidic acid |
| capric acid | heptadecanoic acid | lauric acid |
| lignoceric acid | linoleic add | myristic acid |
| octadecanol | oleic acid | palmitic acid |
| palmitoleic acid | pelargonic acid | pentadecanoic acid |
| squalene | stearic acid | |
| Organic acids | | |
| 2-hydroxyvalerate | 2-ketoadipate | 3-hydroxypropionate |
| adipate | aspartate | β-hydroxybutyrate |
| fumarate | galactonate | γ-aminobutyrate |
| glycerate | glycolate | lactate |
| malate | oxalate | oxamate |
| phenylacetate | phthalate | pyrrole-2-carboxylate |
| pyruvate | salicylate | succinate |
| terephtalic acid | | |
| Sugars and sugaralcohols | | |
| 1,5-anhydroglucitol | arabitol | cellobiose |
| fructose | fucose | galactose |
| glucose | glycerol | lactulose |
| levoglucosan | lyxose | mannitol |
| mannose | myo-inositol | ononitol |
| putrescine | sucrose | threitol |
| threose | xylose | |
| Phosphates | | |
| glycerol-1-phosphate | phosphate | |
| Others | | |
| 1,2,4-benzenetriol | nicotinamide | urea |
| polysiloxane | | |

TABLE 6

| Metabolites | Exponential_Loading 1 | Exponential_Loading 2 | Stationary_Loading 1 | Stationary_Loading 2 |
|---|---|---|---|---|
| 1,2,4-benzenetriol | −0.139 | −0.004 | −0.043 | 0.132 |
| 1,5-anhydroglucitol | −0.087 | −0.141 | −0.165 | −0.103 |
| 1-monopalmitin | −0.160 | 0.019 | 0.054 | −0.189 |
| 1-monostearin | −0.089 | −0.093 | 0.171 | −0.137 |
| 2-hydroxypyridine | −0.140 | 0.153 | −0.144 | −0.138 |
| 2-hydroxyvalerate | −0.045 | −0.259 | −0.064 | −0.145 |
| 2-ketoadipate | −0.081 | −0.025 | −0.124 | −0.036 |
| 3-hydroxypropionate | −0.137 | −0.011 | 0.083 | −0.178 |
| 3-hydroxypyridine | −0.153 | 0.036 | −0.152 | −0.133 |
| 5-aminovaleric acid | −0.133 | −0.025 | −0.111 | −0.170 |

TABLE 6-continued

| Metabolites | Exponential_Loading 1 | Exponential_Loading 2 | Stationary_Loading 1 | Stationary_Loading 2 |
|---|---|---|---|---|
| adipate | −0.133 | −0.152 | −0.107 | −0.043 |
| alanine | 0.135 | −0.021 | 0.051 | 0.093 |
| arabitol | −0.125 | −0.101 | −0.031 | −0.079 |
| arachidic acid | −0.111 | −0.150 | −0.153 | 0.097 |
| aspartate | 0.023 | 0.013 | −0.030 | −0.077 |
| β-alanine | −0.129 | 0.138 | 0.035 | −0.181 |
| β-hydroxybutyrate | −0.074 | 0.110 | −0.006 | −0.049 |
| capric acid | −0.145 | 0.123 | −0.196 | 0.073 |
| carnitine | −0.094 | −0.177 | 0.047 | −0.123 |
| cellobiose | −0.114 | 0.194 | 0.080 | −0.206 |
| fructose | −0.119 | −0.028 | −0.108 | −0.071 |
| fucose | −0.113 | 0.102 | 0.078 | −0.059 |
| fumarate | −0.043 | −0.137 | −0.194 | −0.035 |
| galactonate | −0.041 | −0.070 | 0.000 | −0.051 |
| galactose | −0.054 | −0.108 | −0.153 | −0.117 |
| γ-aminobutyrate | −0.122 | 0.086 | 0.099 | −0.185 |
| glucose | −0.050 | −0.119 | −0.150 | −0.122 |
| glutamate | 0.030 | 0.087 | −0.099 | −0.126 |
| glycerate | −0.139 | −0.070 | −0.160 | −0.100 |
| glycerol | −0.155 | 0.061 | −0.172 | 0.102 |
| glycerol-1-phosphate | 0.044 | 0.151 | −0.040 | −0.102 |
| glycolate | −0.138 | 0.117 | −0.190 | −0.057 |
| heptadecanoic acid | −0.160 | 0.001 | −0.076 | −0.046 |
| hypoxanthine | 0.041 | −0.053 | 0.024 | 0.072 |
| isoleucine | 0.079 | 0.035 | 0.045 | 0.074 |
| lactate | −0.137 | 0.095 | −0.135 | 0.011 |
| lactulose | −0.062 | −0.120 | 0.023 | −0.011 |
| lauric acid | −0.155 | 0.017 | −0.182 | 0.068 |
| leucine | 0.081 | 0.041 | 0.005 | 0.085 |
| levoglucosan | −0.091 | −0.176 | −0.036 | 0.003 |
| lignoceric acid | −0.134 | 0.045 | 0.151 | −0.109 |
| linoleic acid | −0.122 | 0.067 | −0.039 | 0.076 |
| lyxose | −0.064 | −0.059 | −0.092 | −0.051 |
| malate | −0.118 | 0.113 | −0.166 | −0.043 |
| mannitol | −0.125 | −0.095 | −0.122 | 0.010 |
| mannose | −0.068 | −0.110 | −0.103 | −0.065 |
| methionine | 0.066 | 0.036 | −0.040 | −0.002 |
| myo-inositol | −0.094 | 0.107 | 0.011 | −0.129 |
| myristic acid | −0.154 | −0.022 | −0.195 | 0.070 |
| nicotinamide | −0.031 | −0.122 | −0.021 | −0.050 |
| octadecanol | −0.167 | 0.030 | −0.018 | −0.145 |
| oleic acid | −0.110 | −0.025 | −0.105 | −0.007 |
| ononitol | −0.075 | −0.015 | −0.062 | 0.051 |
| ornithine | 0.019 | −0.077 | 0.013 | −0.045 |
| oxalate | −0.144 | 0.100 | 0.043 | −0.212 |
| oxamate | −0.127 | 0.166 | −0.119 | −0.053 |
| oxoproline | −0.105 | 0.190 | 0.022 | −0.216 |
| palmitic acid | −0.131 | −0.132 | −0.202 | 0.028 |
| palmitoleic acid | −0.098 | 0.112 | −0.092 | 0.02.3 |
| pelargonic acid | −0.1.39 | 0.108 | −0.199 | 0.057 |
| pentadecanoic acid | −0.138 | −0.041 | −0.074 | −0.007 |
| phenylacetate | −0.090 | 0.117 | 0.095 | −0.205 |
| phenylalanine | 0.069 | 0.058 | −0.097 | −0.036 |
| phosphate | −0.027 | −0.182 | −0.045 | −0.206 |
| phthalate | −0.151 | 0.035 | 0.116 | −0.086 |
| proline | −0.006 | 0.148 | 0.135 | −0.137 |
| putrescine | −0.069 | 0.216 | 0.057 | −0.192 |
| pyrrole-2-carboxylate | 0.004 | 0.091 | −0.043 | −0.178 |
| pyruvate | −0.142 | 0.025 | −0.125 | −0.090 |
| salicylate | −0.040 | 0.072 | −0.018 | −0.060 |
| serine | −0.112 | 0.098 | −0.094 | −0.021 |
| squalene | −0.101 | 0.082 | 0.071 | −0.100 |
| stearic acid | −0.145 | −0.128 | −0.186 | 0.012 |
| succinate | −0.133 | 0.107 | −0.061 | −0.212 |
| sucrose | −0.044 | 0.003 | −0.092 | −0.007 |
| terephthalic acid | −0.150 | 0.032 | −0.117 | −0.084 |
| threitol | −0.123 | −0.071 | 0.016 | 0.036 |
| threonine | 0.111 | 0.151 | 0.031 | 0.073 |
| threose | −0.085 | −0.227 | 0.004 | 0.169 |
| thymine | 0.076 | 0.195 | 0.071 | −0.074 |
| tryptophan | 0.061 | 0.064 | 0.018 | −0.076 |
| uracil | 0.110 | −0.024 | 0.164 | −0.124 |
| urea | 0.140 | 0.040 | 0.113 | −0.044 |
| valine | 0.089 | 0.038 | 0.111 | 0.085 |
| xylose | −0.092 | −0.140 | −0.014 | −0.124 |

Figure 7:
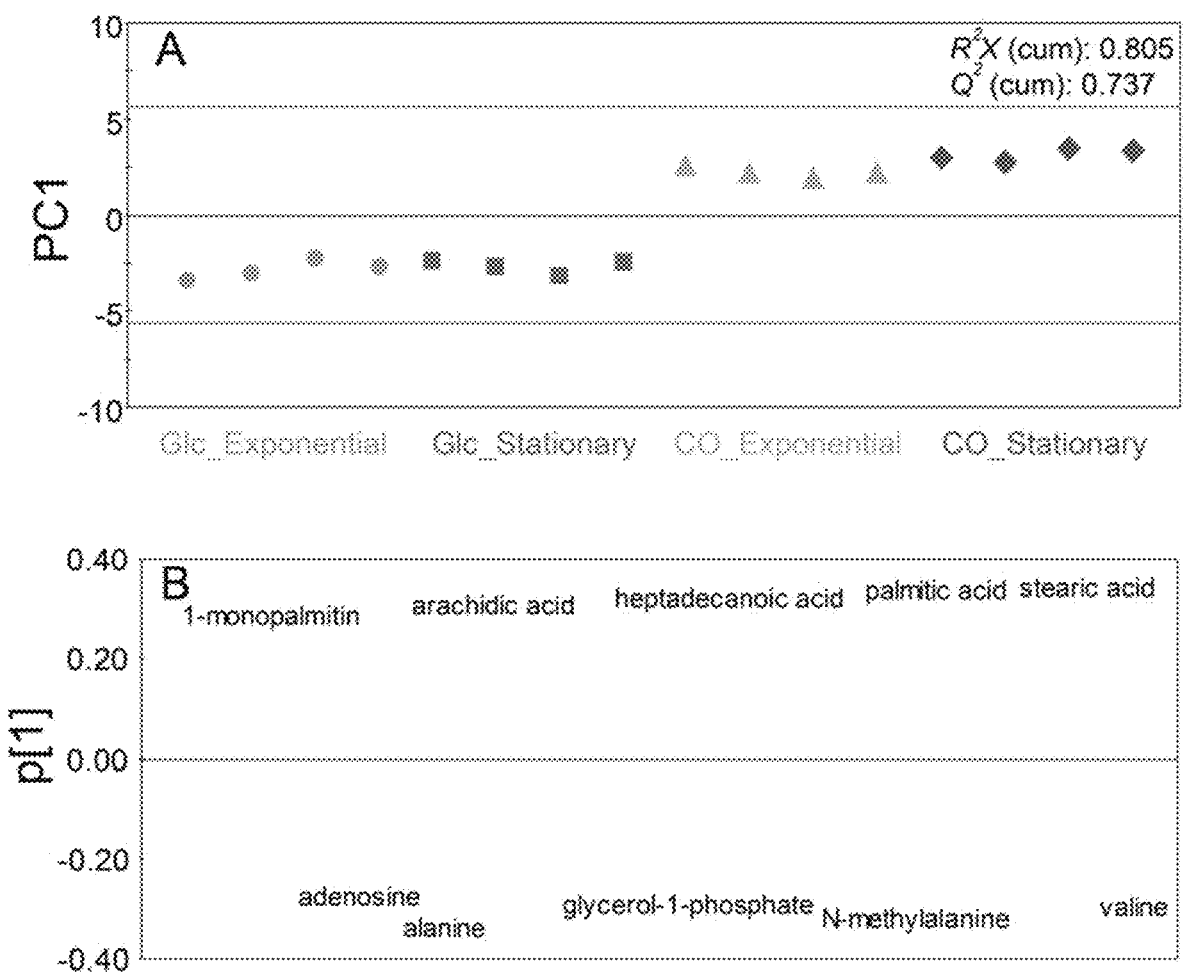
FIG. 7 illustrates models (Glc_Exponential: a metabolomic analysis result of the exponential phase in the glucose culture; Glc_Stationary: a metabolomic analysis result of the stationary phase in the glucose culture; CO_Exponential: a metabolomic analysis result of the exponential phase in the synthetic gas culture; CO_Stationary: a metabolomic analysis result of the stationary phase in the synthetic gas culture, A: score plot; B: loading plot) classifying the glucose culture and the synthetic gas culture employing 10 main metabolomes as variables during the glucose culture and the synthetic gas culture of the synthetic gas fermentation microorganisms using PCA.
Figure 8:
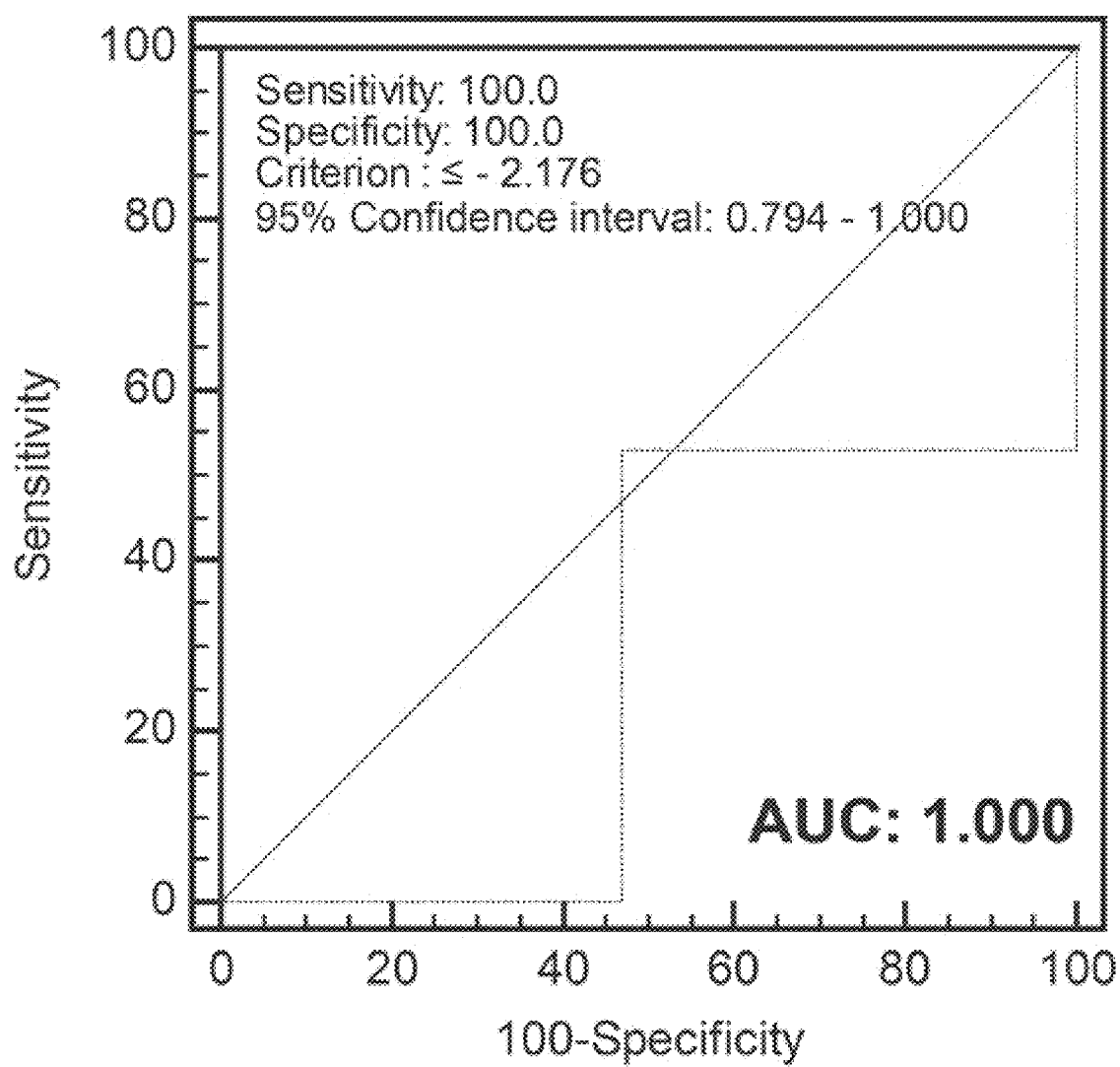
FIG. 8 verifies a PCA model classifying the glucose culture and the synthetic gas culture employing 10 main metabolomes as variables during the glucose culture and the synthetic gas culture of the synthetic gas fermentation microorganisms using a ROC curve.

Example 4: Selection of Main Metabolite and Verification of Distinction Between Glucose Culture and Synthetic Gas Culture Using the Same In order to completely classify a glucose culture and a synthetic gas culture of a synthetic gas fermentation strain using 10 representative metabolites showing a difference in the glucose culture and the synthetic gas culture of the synthetic gas fermentation strain selected from Example 2, a PCA model was generated (FIG. 7). For the PCA model generated by the 10 metabolites, the metabolomic profiles during the synthetic gas culture and the glucose culture exhibited positive values and negative values, respectively, based on the PCI axis, and were completely classified (A of FIG. 7). A loading plot was used to show how the 10 metabolites were involved in the PCA model (B of FIG. 7). Further, a ROC curve was applied to examine whether the classification model was statistically significant (FIG. 8). As a result, through sensitivity 100%, specificity 100%, and AUC 1.000, it could be verified that the PCA model for classifying the glucose culture and the synthetic gas culture of the synthetic gas fermentation strain generated by the 10 metabolites was very statistically significant.

The invention claimed is:

1. A method for analyzing metabolomic differentiation for distinguishing a glucose culture and a synthetic gas culture of *Clostridium carboxidivorans*, the method comprising:
    a metabolome sampling step of subjecting a biological sample of *Clostridium carboxidivorans* to fast filtration under an aerobic condition, washing the filtrate with water, and then extracting a metabolome using a mixed solvent of water, 2-propanol, and methanol at a volume ratio of 2:2:5 as an extraction solvent.

* * * * *